United States Patent [19]

Markin et al.

[11] Patent Number: 5,417,922

[45] Date of Patent: May 23, 1995

[54] SPECIMEN CARRIER

[75] Inventors: Rodney S. Markin, Omaha, Nebr.; Eldon L. Tackett, Neola, Iowa; Stephen J. Hoskinson, Omaha, Nebr.

[73] Assignee: Board of Regents - University of Nebraska, Lincoln, Nebr.

[21] Appl. No.: 62,785

[22] Filed: May 14, 1993

[51] Int. Cl.⁶ ................................................ B01L 9/06
[52] U.S. Cl. .................................. 422/65; 422/104; 198/465.2; 211/74
[58] Field of Search ............ 422/102, 104, 65, 64; 206/446, 443, 459.5; 436/47, 48, 49; 211/74; 198/465.2, 795, 836.1; 220/507

[56] References Cited

U.S. PATENT DOCUMENTS

| | | | |
|---|---|---|---|
| 3,578,412 | 5/1971 | Martin | 436/47 |
| 3,666,082 | 5/1972 | Riggs | 198/836.1 |
| 3,916,157 | 10/1975 | Roulette et al. | 422/65 |
| 4,022,579 | 5/1977 | Reuillet et al. | 211/74 |
| 4,040,533 | 8/1977 | De Boer et al. | 198/465.2 |
| 4,218,534 | 8/1980 | LaBelle et al. | 435/5 |
| 4,389,374 | 6/1983 | Sutton et al. | 422/102 |
| 4,454,939 | 6/1984 | Kampf et al. | 198/465.2 |
| 4,510,119 | 4/1985 | Hevey | 422/104 |
| 4,534,465 | 8/1985 | Rothermal et al. | 211/74 |
| 4,727,033 | 2/1988 | Hijikata et al. | 422/65 |
| 4,770,854 | 9/1988 | Lyman | 435/296 |
| 4,938,369 | 7/1990 | Carilli | 211/74 |
| 5,011,779 | 4/1991 | Maimon | 422/104 |
| 5,069,336 | 12/1991 | Mauthe | 206/219 |
| 5,186,339 | 2/1993 | Heissler | 422/104 |

FOREIGN PATENT DOCUMENTS

| | | | |
|---|---|---|---|
| 8300102 | 1/1983 | European Pat. Off. | 422/102 |
| 3934088 | 4/1991 | Germany | 422/102 |

Primary Examiner—Robert J. Warden
Assistant Examiner—Theresa T. Snider
Attorney, Agent, or Firm—Zarley, McKee, Thomte, Voorhees & Sease; Mark D. Frederiksen

[57] ABSTRACT

A specimen carrier for transporting conventional specimen tubes throughout an automatic laboratory conveyance system includes a generally rectilinear carrier body with a forward face having an identification zone delimited thereon. An identification code is marked in the identification zone so as to permit mechanical sensing and identification of the carrier on a conveyor system. A plurality of holes of various diameters and depths are provided in the top surface of the carrier to receive conventional specimen tubes of various types with the top ends of the specimen tubes located at a predetermined height above the top surface of the carrier.

2 Claims, 3 Drawing Sheets

SPECIMEN CARRIER

TECHNICAL FIELD

The present invention relates generally to apparatus for carrying laboratory specimens, and more particularly to a carrier for transporting test tubes with specimens therein.

BACKGROUND OF THE INVENTION

Clinical laboratory testing has changed and improved remarkably over the past 70 years. Initially, tests or assays were performed manually, and generally utilized large quantities of serum, blood or other materials/body fluids. As mechanical technology developed in the industrial work place, similar technology was introduced into the clinical laboratory. With the introduction of new technology, methodologies were also improved in an effort to improve the quality of the results produced by the individual instruments, and to minimize the amount of specimen required to perform each test.

More recently, instruments have been developed to increase the efficiency of testing procedures by reducing turnaround time and decreasing the volumes necessary to perform various assays. Present directions in laboratory testing focus on cost containment procedures and instrumentation. Laboratory automation is one area in which cost containment procedures are currently being explored. Robotic engineering has evolved to such a degree that various types of robots have been applied in the clinical laboratory setting.

The main focus of prior art laboratory automation relies on the implementation of conveyor systems to connect areas of a clinical laboratory. Known conveyor systems in the laboratory setting utilize separate conveyor segments to move specimens from a processing station to a specific laboratory work station. In order to obtain cost savings, the specimens are sorted manually, and test tubes carrying the specimens are grouped in a carrier rack to be conveyed to a single specific location. In this way, a carrier will move a group of 5-20 specimens from a processing location to a specific work station for the performance of a single test on each of the specimens within the carrier rack.

With the advent of the inventor's new laboratory automation system as described in co-pending patent application Ser. No. 07/997,281, entitled "METHOD FOR AUTOMATIC TESTING OF LABORATORY SPECIMENS" the inventor has provided a laboratory automation system which requires a different type of specimen carrier. Because the new laboratory automation system of the co-pending patent application calls for identification and conveyance of an individual patient's specimens throughout the laboratory system, it is no longer feasible to utilize conventional specimen tube carrier racks.

Conventional specimen tube carrier racks suffer several drawbacks when considering use in the inventor's new laboratory automation system. First, prior art carrier racks were designed to hold a single type of specimen tube within a rack. Thus, more than one rack would be required for different sizes and types of specimen tubes.

Also, it was not possible to identify the specimen rack and correlate specific test tubes with an individual rack, for independent conveyance throughout a laboratory system.

Finally, in the automated laboratory setting, prior art racks were not provided with structure for permitting separation of the racks for individual guidance through a conveyor system.

SUMMARY OF THE INVENTION

It is therefore a general object of the present invention to provide an improved specimen carrier for use with a laboratory automation system.

Another object of the present invention is to provide a specimen carrier which will receive a plurality of test tube types in a standardized and uniform arrangement.

Still another object is to provide a specimen carrier with a forward identification surface permitting automated identification of the carrier on a conveyor system.

A further object of the present invention is to provide a specimen carrier which permits individual retention and guidance even when stacked in a line of carriers.

These and other objects will be apparent to those skilled in the art.

The specimen carrier of the present invention is designed for transporting conventional specimen tubes throughout an automatic laboratory conveyance system. The specimen carrier includes a generally rectilinear carrier body with a forward face having an identification zone delimited thereon. An identification code is marked in the identification zone so as to permit mechanical sensing and identification of the carrier on a conveyor system. A plurality of holes of various diameters and depths are provided in the top surface of the carrier to receive conventional specimen tubes of various types. Because the carrier is designed for use on an automatic laboratory system, various types of specimen tubes must be disposed within the specimen carrier such that the top end of the specimen tube is located at a predetermined height above the top surface of the carrier. This permits automatic retraction of the specimen tube by other robotic devices. A groove on the rear face of the carrier body is oriented horizontally along the body to permit the carrier body to move along the conveyor track past a projecting pin corresponding with a groove. The groove prevents the carrier body from being placed in a reverse orientation on the conveyor wherein a sensor would be unable to read the identification code.

DESCRIPTION OF THE PREFERRED EMBODIMENT

Figure 1:
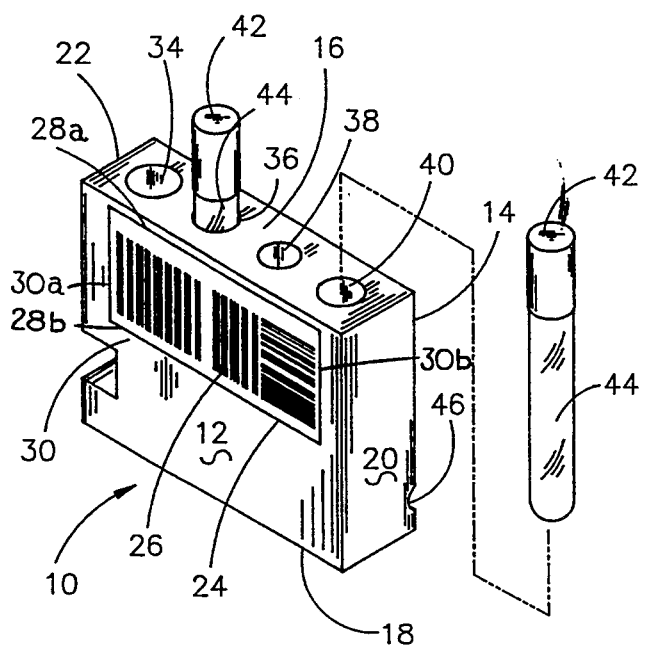
FIG. 1 is a front perspective view of the specimen carrier of the present invention.
Figure 5:
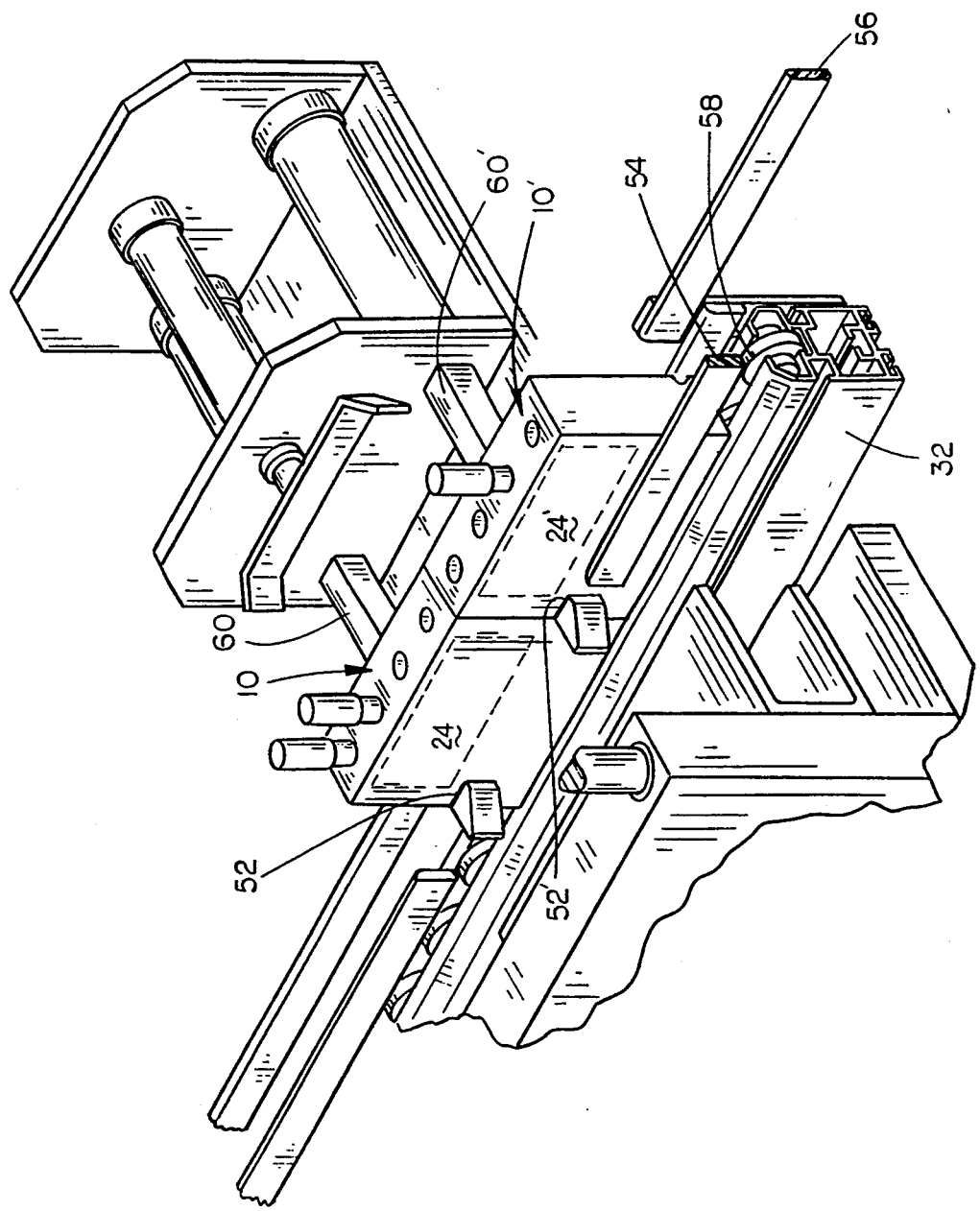
FIG. 5 is a pictorial view of two specimen carriers being transported on an automatic conveyor system.

Referring now to the drawings, in which similar or corresponding parts are identified with the same reference numeral, and more particularly to FIG. 1, the specimen carrier of the present invention is designated generally at 10 and is preferably formed of a solid lightweight block of plastic material. Carrier 10 includes a forward face 12, a rearward face 14, top surface 16, bottom surface 18, and right and left end walls 20 and 22, respectively. Forward face 12 has an identification zone 24 located thereon, on which an identification code 26, shown in FIG. 1 as printed bar code is located. Identification zone 24 has top and bottom boundaries 28a and 28b located a predetermined distance down from top surface 16, and left and right boundaries 30a and 30b located a predetermined distance from left end wall 22 and right end wall 20, respectively. In this way, when a plurality of specimen carriers 10 are aligned on a conveyor track 32, as shown in FIG. 5, a sensor, such as a bar code reader (not shown) can determine the beginning and end of any identification code located within identification zone 24. In addition, bar code 26 may be oriented both horizontally and vertically (as shown), so that a sensor may be conveniently oriented in either direction.

Figure 2:
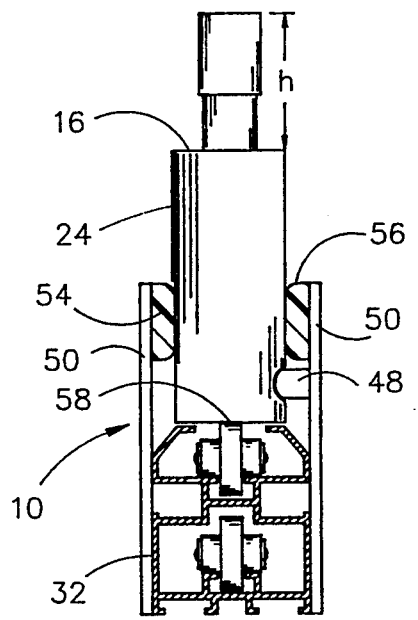
FIG. 2 is an end elevational view of the specimen carrier mounted on a conveyor track.
Figure 3:
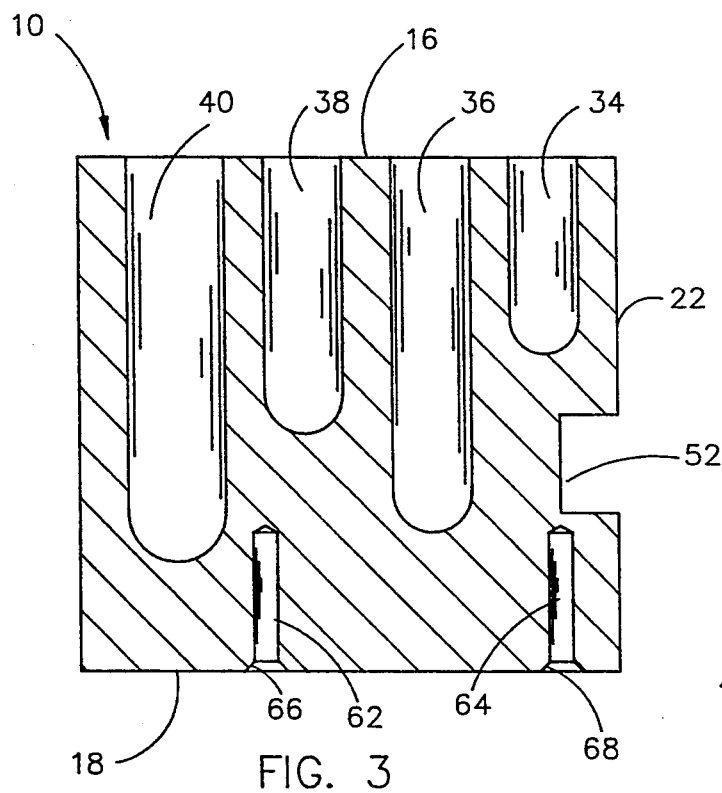
FIG. 3 is a sectional view taken at lines 3—3 in FIG. 4.

Referring to FIGS. 1 and 3, four holes, 34, 36, 38 and 40 are formed in top surface 16 and extend downwardly towards bottom surface 18 predetermined distances. Preferably, first hole 34 is approximately 7/16 inch in diameter and has a depth of approximately 1.3 inches. Hole 36 is approximately ½ inch in diameter and has a depth of approximately 2.5 inches. Third hole 38 has a diameter of about ½ inch and a depth of approximately 1.8 inches. Finally, fourth hole 40 has a diameter of about ⅝ inch and a depth of approximately 2.6 inches. The diameters and depths of holes 34-40 are determined for specific types of specimen tubes commonly utilized in the medical field. The varying depths of holes 34-40 are necessary in order to maintain a standard height "H" of the top 42 of test tube 44 above top surface 16 of carrier 10, as shown in FIG. 2. This standard height "H" is particularly critical in automated laboratory systems because the automated functions of various equipment is based upon this standard dimension. For example, a robotic arm utilized to remove a test tube 44 from specimen carrier 10 will be programmed to grip a test tube at a particular location within height "H" to remove the test tube from the carrier. The robotic arm will also rely on the location of the grip on the test tube for relocating the test tube at the particular apparatus utilized to conduct a test on a specimen within the test tube. If the upper end 42 of test tube 44 is not within a predetermined dimension, a robotic arm could easily break the test tube or incorrectly align a test tube within the scientific instrument.

Furthermore, the conveyor system for specimen carriers 10 utilizes standard clearances to permit travel of specimen carriers around the conveyor on track 32. Without a standardized height, it may be difficult or impossible to utilize the specimen carrier 10 on the conveyor system, since the required clearance may not be met.

As discussed above, identification zone 24 provides a space for an ID code to permit an automated laboratory system to identify the specimen carrier and route the carrier throughout the conveyor system as required for the specimens within the carrier. In order to avoid requiring sensors on both sides of the conveyor track 32, specimen carrier 10 is provided with a groove 46 extending horizontally along the rearward face 14 of carrier 10. Groove 46 corresponds with a projecting pin 48 mounted on a rear guide rail support arm 50 at individual work stations. In this way, after the testing of a specimen has been completed, specimen carrier 10 is inserted on track 32 and must move past pin 48 to continue on the conveyor system. If specimen carrier 10 is oriented correctly, groove 46 will permit carrier 10 to move past pin 48. If carrier 10 is reversed, pin 48 will prevent passage of the specimen carrier 10. In this way, forward face 12 of carrier 10 is always directed outwardly to permit sensing by a sensor.

As shown in FIG. 1, identification zone 24 has a lower boundary 28b spaced from top surface 16, and upper, left and right boundaries 28a, 30a and 30b, located relative to top wall 16, left end wall 22 and right end wall 20. Lower boundary 28b is located a distance below top surface 16 which corresponds to the height of the forward guard rail 54, as shown in FIGS. 2 and 5, so that bar code 26 may be sensed by a sensor located above guard rail 54.

Forward and rearward guard rails 54 and 56, are supported on support arms 50 above the transport surface 58 of track 32. Guard rails 54 and 56 are spaced apart to permit movement of carrier 10 therebetween, and are spaced above transport surface 58 to permit a sensor to scan identification zone 24.

Figure 4:
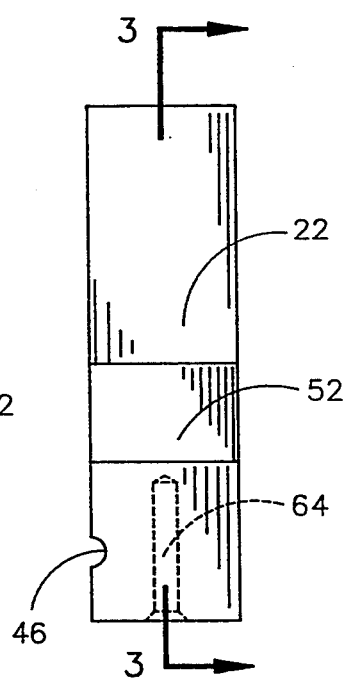
FIG. 4 is an end elevational view taken from the left end of FIG. 1.

Referring now to FIGS. 3 and 4, a generally rectangular notch 52 is formed in left end wall 22. Notch 52 is located so as to receive an extendable arm 60 therethrough, as shown in FIG. 5. The laboratory automation system includes gates and elevators to remove a specimen carrier 10 from the conveyor track 32, to redirect specimen carrier 10 to a secondary track or various work station.

FIG. 5 shows two specimen carriers 10 and 10' retained in a stationary position by extendable arm 60 and a second extendable arm 60'. Notch 52' on carrier 10' permits arm 60' to extend between carriers 10 and 10' to retain specimen carrier 10' in position until carrier 10 is redirected to an appropriate location.

Referring now to FIGS. 3 and 4, a pair of spaced apart apertures 62 and 64 extend vertically upwardly in bottom surface 18. Each aperture 62 and 64 has an annular chamfer 66 and 68 respectively, forming a conical shape into each aperture, for a purpose described in more detail hereinbelow.

Figure 6:
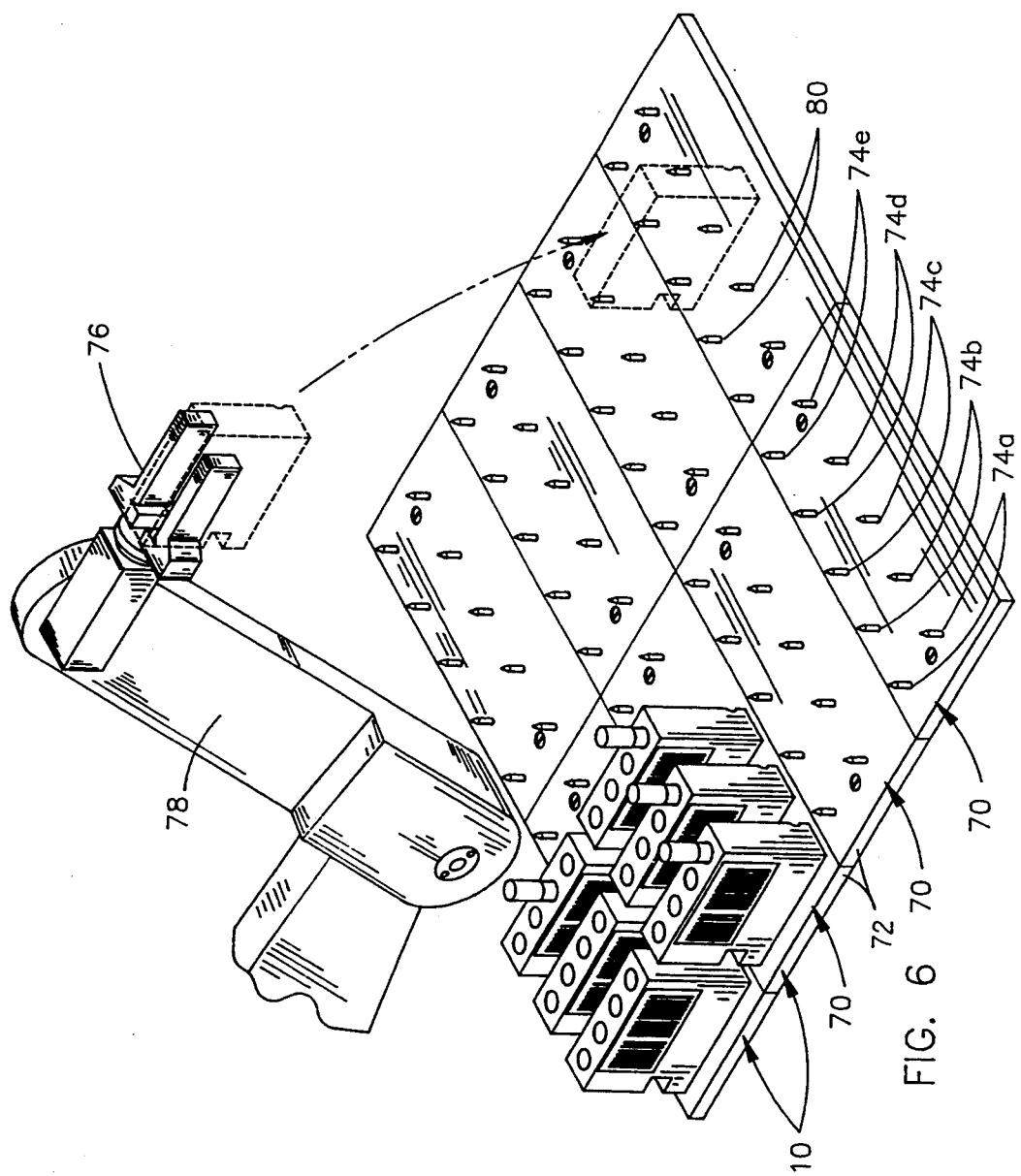
FIG. 6 is a perspective view of specimen carrier storage racks and a robotic arm for placement thereon.

Specimen carrier 10 may be temporarily stored on storage racks 70, as shown in FIG. 6. Each storage rack 70 includes a base plate 72 with a plurality of locator pins 74 projecting upwardly from the upper surface of base plate 72. Locator pins 74 are arranged in sets of pairs 74a, 74b, 74c, 74d and 74e, each set of pins being longitudinally spaced apart so as to correspond with the pair of apertures 62 and 64 (see FIG. 3) on each specimen carrier 10. Pin pairs 74a-74e are spaced apart laterally a distance such that specimen carriers 10 are laterally spaced apart to permit the specimen carrier to be grasped by the jaws 76 of a robot arm 78.

The laboratory automation system for which the specimen carriers 10 are designed includes robot arms at various work stations which will remove a specimen tube from the specimen carrier for further processing. For those work stations which permit processing of more than one specimen tube at a time, it is desirable to locate the individual specimen carriers in a defined position where the robot arm 78 can easily locate the appropriate specimen carrier. While such robotics are very accurate, movement of the specimen carrier from vibration or other external forces, could prevent the robot arm from locating and retrieving the specimen carrier, or from accurately positioning a test tube into the appropriate specimen carrier.

Locator pins 80 are preferably formed with a conical point 80 at their upper end to assist in precisely locating a specimen carrier 10 on the base plates 72. Conical chamfers 66 and 68 formed in apertures 62 and 64, respectively, assist in this placement, so as to direct the specimen carrier 10 on the locator pins, despite minor misalignment of the specimen carrier with the locator pins.

A plurality of storage racks 70 may be mounted on a surface adjacent the robot arm 78 as desired to locate and store specimen carrier 10, as shown in FIG. 6.

Whereas the invention has been shown and described in connection with the preferred embodiment thereof, it will be understood that many modifications, substitutions and additions may be made which are within the intended broad scope of the appended claims. For example, the number and size of holes within the specimen carrier is determined only by the variety of the specimen tube types that are desired to be utilized in the laboratory automation system. Similarly, while a conventional bar code is shown for the identification code, various other types of identification code materials could be utilized in printed format or otherwise.

Therefore, there has been shown and described an improved specimen carrier which accomplishes at least all of the above stated objects.

I claim:

1. In combination:
   a plurality of specimen carriers for transporting a laboratory specimen carried within a specimen tube, each specimen carrier comprising:
      a carrier body having a forward face, rearward face, top surface, bottom surface, right end wall and left end wall;
      specimen tube carrying means on said carrier body for carrying at least one specimen tube in a generally upright position and with the upper end of the specimen tube located a predetermined height above the top surface of said carrier body; and
      a first half of cooperable means for retaining said specimen carrier at a predetermined location on a storage rack, on the bottom surface of said specimen carrier; and
   each of said specimen carriers being independently and removably retained on a storage rack;
      said storage rack supporting a plurality of specimen carriers at predetermined locations, comprising:
         a generally planar base plate having an upper surface; and
         a second half of said cooperable means for retaining said plurality of specimen carriers on the upper surface of said base plate;
   said first half of said cooperable means including a generally vertical aperture formed in the bottom surface of each said specimen carrier body, and said second half of said cooperable means including a plurality of pins projecting upwardly from said base plate upper surface having dimensions to permit removable receipt within said carrier body apertures, such that each carrier body is individually and independently removable from said storage rack;
   said cooperable means on said specimen carriers and rack permitting independent removal of each specimen carrier from the rack.

2. In combination:
   a conveyor, including:
      an elongated conveyor track with an operable transport surface for moving a body supported thereon in a longitudinal direction; and
      forward and rearward spaced apart and parallel guide rails connected to said track and extending longitudinally therealong for guiding a body located between the guide rails and supported on the transport surface; and
   a specimen carrier transported on said conveyor, comprising:
      a carrier body having a forward face, rearward face, top surface, bottom surface, right end wall and left end wall;
      said forward face having an identification zone delimited by a lower boundary spaced a predetermined distance above the bottom surface of the carrier body;
      identification code means on said forward face within said identification zone, identifying the specimen carried by the carrier body; and
      specimen tube carrying means on said carrier body for carrying at least one specimen tube in a generally upright position and with the upper end of the specimen tube located a predetermined height above the top surface of said carrier body;
   said carrier body having a depth, as measured between the forward and rearward faces less than the distance between said guide rails, to permit free movement of the carrier body longitudinally on the track transport surface;
   said carrier body oriented on said conveyor track with the forward and rearward faces generally parallel and adjacent the forward and rearward guide rails;
   a selectively extendible arm operably mounted on said track for selected movement between an extended position, extending transversely across the longitudinal axis of the track and spaced a predetermined distance above the track transport surface, to engage a portion of the left end wall to prevent longitudinal movement and a retracted position permitting longitudinal movement of said specimen carrier on the track; and
   said carrier body having a notch formed in the left end wall and extending from the forward face to the rearward face, having dimensions to receive said arm therein such that said arm does not project outwardly beyond the left end wall when extended through said notch.

* * * * *